United States Patent
Abe (10) Patent No.: US 7,163,509 B2
(45) Date of Patent: Jan. 16, 2007

(54) COMPONENT OF ENDOSCOPE AND ENDOSCOPE PROVIDED WITH THE COMPONENT

(75) Inventor: Masanao Abe, Saitama (JP)

(73) Assignee: PENTAX Corporation, Tokyo (JP)

( * ) Notice: Subject to any disclaimer, the term of this patent is extended or adjusted under 35 U.S.C. 154(b) by 113 days.

(21) Appl. No.: 10/737,891

(22) Filed: Dec. 18, 2003

(65) Prior Publication Data
US 2004/0176660 A1 Sep. 9, 2004

(30) Foreign Application Priority Data
Dec. 19, 2002 (JP) ............................. 2002-369059

(51) Int. Cl.
*A61B 1/04* (2006.01)
(52) U.S. Cl. ...................... 600/117; 430/320; 430/346; 430/945
(58) Field of Classification Search ................ 600/104, 600/117, 143, 151; 430/320, 346, 945
See application file for complete search history.

(56) References Cited

U.S. PATENT DOCUMENTS

| | | | | |
|---|---|---|---|---|
| 4,951,686 A | * | 8/1990 | Herlitze | ...................... 600/585 |
| 5,084,022 A | * | 1/1992 | Claude | ................... 604/164.13 |
| 5,454,881 A | * | 10/1995 | Fischer | ........................ 148/241 |
| 6,719,685 B1 | * | 4/2004 | Fujikura et al. | ............. 600/114 |
| 6,811,958 B1 | * | 11/2004 | Iwami et al. | ................ 430/320 |
| 2002/0087098 A1 | | 7/2002 | Iwani et al. | |

FOREIGN PATENT DOCUMENTS

| | | |
|---|---|---|
| JP | 2582680 | 7/1998 |
| JP | 2002-119599 | 4/2002 |
| JP | 2002-136600 | 5/2002 |
| JP | 2002-188016 | 7/2002 |
| JP | 2002-283729 | 10/2002 |

* cited by examiner

*Primary Examiner*—Linda C. M. Dvorak
*Assistant Examiner*—Matthew J. Kasztejna
(74) *Attorney, Agent, or Firm*—Greenblum & Bernstein, P.L.C.

(57) ABSTRACT

A component of an endoscope is a flexible tube which is composed of a helical coil, a reticular tube formed of a braided thin wires and provided over the helical coil, and an outer cover provided over the reticular tube. The outer cover is formed of a resin material containing $TiN_xO_y$, (where, $0.1 \leq x \leq 1.0$, $0 \leq y \leq 1.9$) which is a color developing agent to be colored when irradiated with laser light. The flexible tube is provided with scale formed by the colored portion. The outer surface the outer cover is black or dark color before the irradiation with laser light, but thus formed scale is white or blight color having a whiteness of 60% or more.

11 Claims, 5 Drawing Sheets

Fig. 5

COMPONENT OF ENDOSCOPE AND ENDOSCOPE PROVIDED WITH THE COMPONENT

BACKGROUND OF THE INVENTION

1. Field of the Invention

This invention relates to a component of an endoscope and an endoscope provided with the component.

2. Description of the Prior Art

In the field of medicine, endoscopes are widely used for examination or diagnosis of digestive tracts and the like. Such endoscope includes a flexible tube (insertion section) to be inserted into a body cavity and an operating section for operating the flexible tube. The operating section includes operating knobs for carrying out bending operations of the tip part of the flexible tube.

In such endoscopes, various indications are provided as indexes (visible markers) which are used when an operator inserts the flexible tube into the body cavity or carries out operations of the operating section. For example, scale is provided on the flexible tube for indicating the insertion depth of the flexible tube, and symbols or letters or the like are provided on the operating knobs for indicating directions toward which the tip part of the flexible tube is to be bent by the operation of the operating knobs.

Conventionally, such indications are formed by printing with ink (see, for example, Japanese Utility Model Publication No. 2582680) or laser processing or the like.

However, the method using printing with ink involves several problems. For example, it is difficult to form indication onto a curved surface, it takes a certain time until the ink is dried, and there is a risk that the ink layer is peeled off from the component during its use to be eluted into a body cavity, and the like.

Further, in the method using laser processing, grooves are formed on the component and thus formed grooves are used as indication. Accordingly, there is a case that sufficient contrast cannot be obtained between the grooves and the part other than the grooves, which results in the problem in that thus formed indication has relatively poor visibility as compared with the indication formed by the ink. In addition, when the endoscope provided with the indication of this type is disinfected and sterilized, disinfectant solution likely remains within the grooves, so that there is a fear that deterioration will be caused therefrom.

SUMMARY OF THE INVENTION

In view of the problems in the conventional methods described above, it is an object of the present invention is to provide a component of an endoscope and an endoscope provided with the component having a colored portion which has good visibility and in which peel-off, fade-away and color deterioration are difficult to occur.

In order to achieve the above object, the present invention is directed to a component of an endoscope, comprising an outer surface formed with a colored portion, the colored portion being formed by means of development of a color developing agent, wherein the color developing agent comprising $TiN_xO_y$ (where, $0.1 \leq x \leq 1.0$, $0 \leq y \leq 1.9$) which is developed by radiation with laser light, and the color developing agent is contained at least in a part of the component which is in the vicinity of the outer surface thereof.

According to the present invention having the above structure, it is possible to provide a component of an endoscope having a colored portion which provides excellent visibility and in which peel-off, fade-away and color deterioration of the colored portion are also difficult to occur.

In the present invention, it is preferred that at least the part of the component in the vicinity of the outer surface thereof is mainly formed of a resin material.

Further, it is also preferred that the color developing agent is in the form of particles.

This makes it possible to disperse the color developing agent into the part in the vicinity of the outer surface uniformly.

In this case, it is preferred that the average particle size of the particulate color developing agent is 10 µm or less.

This makes it possible to disperse the color developing agent into the part in the vicinity of the outer surface more uniformly.

Further, in the present invention, it is preferred that the content of the color developing agent in the part is 0.01 to 10 weight percent.

This amount makes it possible that the color developing agent is sufficiently contained in the part and that the colored portion has clear visibility.

Furthermore, in the present invention, it is preferred that the color of the colored portion before the irradiation with the laser beam was black or dark color. Further, it is also preferred that the color of the colored portion is white or bright color.

Moreover, in the present invention, it is preferred that the degree of whiteness (L value) of the colored portion is 60% or more. If the whiteness is too small, it is not possible to obtain satisfactory visibility.

Moreover, in the present invention, it is also preferred that the component further comprises a coating layer which is provided so as to cover at least the colored portion and which has transparency through which the colored portion can be seen. According to this arrangement, the coating layer functions as a protective layer, so that peel-off, fade-away and color deterioration of the colored portion can be prevented reliably Further, in the present invention, it is also preferred that the component further comprises a coating layer which is provided so as to cover at least the colored portion and which has transparency through which the colored portion can be seen, and through which the laser light can be passed. According to this arrangement, the coating layer functions as a protective layer, so that peel-off, fade-away and color deterioration of the colored portion can be prevented reliably. Further, it is also possible to prevent the colored portion from being peeled off or damaged even if that portion is scratched.

Moreover, in the present invention, the colored portion is preferably used as a visible maker. This makes it possible to perform reliable operations.

Preferably, in the present invention, the component is a flexible tube of the endoscope.

Another aspect of the present invention is directed to an endoscope which is provided with the component of an endoscope as described above. Such endoscope can have excellent operability.

The present invention further provides an endoscope, comprising: an operating section provided with a plurality of components for manipulating the endoscope; and an elongated flexible tube to be inserted into a body cavity of a living body, the flexible tube having a base end connected to the operating section, and the flexible tube including an outer cover having an outer surface and made of a thermoplastic elastomer providing black or dark color, wherein the outer surface of the outer cover being formed with a colored portion, the colored portion being formed by means of development of a color developing agent, wherein the color developing agent comprising $TiN_xO_y$ (where, $0.1 \leq x \leq 1.0$, $0y \leq 1.9$) which is developed by radiation with laser light to provide white or bright color, and the color developing agent is contained at least in the vicinity of the outer surface of the outer cover, and the content of the color developing agent contained in the outer cover is 3.0 to 10 weight percent of the outer cover.

The present invention further provides an endoscope having a colored portion which provides excellent visibility and in which peel-off, fade-away and color deterioration of the colored portion are also difficult to occur.

Moreover, in the present invention, it is also preferred that the endoscope further comprises a coating layer which is provided so as to cover at least the colored portion and which has transparency through which the colored portion can be seen. According to this arrangement, the coating layer functions as a protective layer, so that peel-off, fade-away and color deterioration of the colored portion can be prevented reliably.

Further, in the present invention, it is also preferred that the endoscope further comprises a coating layer which is provided so as to cover at least the colored portion and which has transparency through which the colored portion can be seen, and through which the laser light can be passed. According to this arrangement, the coating layer functions as a protective layer, so that peel-off, fade-away and color deterioration of the colored portion can be prevented reliably. Further, it is also possible to prevent the colored portion from being peeled off or damaged even if that portion is scratched.

The present invention is also directed to an endoscope wherein the components of the operating section include knobs, levers and/or buttons, and at least one of these components is made of a resin material providing a black or dark color and formed with a colored portion, the colored portion being formed by means of development of a color developing agent, wherein the color developing agent comprises $TiN_xO_y$ (where, $0.1 \leq x \leq 1.0$, $0 \leq y \leq 1.9$) which is developed by irradiation with laser light to provide white or bright color, and wherein the color developing agent is contained at least in the vicinity of the outer surface of the component, and the content of the color developing agent contained in the component is 3.0 to 10 weight percent of the component.

Additionally, the present invention is directed to an endoscope wherein the colored portion of an endoscope is used as a visible maker.

Further, the present invention is directed to an endoscope, comprising an operating section provided with a plurality of components for manipulating the endoscope; and an elongated flexible tube to be inserted into a body cavity of a living body, the flexible tube having a base end connected to the operating section, wherein the components of the operating section include knobs, levers and/or buttons, and at least one of these components is made of a resin material providing a black or dark color and formed with a colored portion, the colored portion being formed by means of development of a color developing agent, wherein the color developing agent comprises $TiN_xO_y$ (where, $0.1 \leq X \leq 1.0$, $0 \leq y \leq 1.9$) which is developed by irradiation with laser light to provide white or bright color, and wherein the color developing agent is contained at least in the vicinity of the outer surface of the component, and the content of the color developing agent contained in the component is 3.0 to 10 weight percent of the component.

Moreover, the present invention is directed to an endoscope wherein the colored portion is used as a visible maker.

These and other objects, structures and results of the present invention will be apparent more clearly when the following detailed description of the preferred embodiments is considered taken in conjunction with the accompanying drawings.

DETAILED DESCRIPTION OF THE INVENTION

Hereinafter, a detailed description of the preferred embodiments of a component of an endoscope and an endoscope equipped with the component according to the present invention will be given with reference to the appended drawings.

Figure 1:
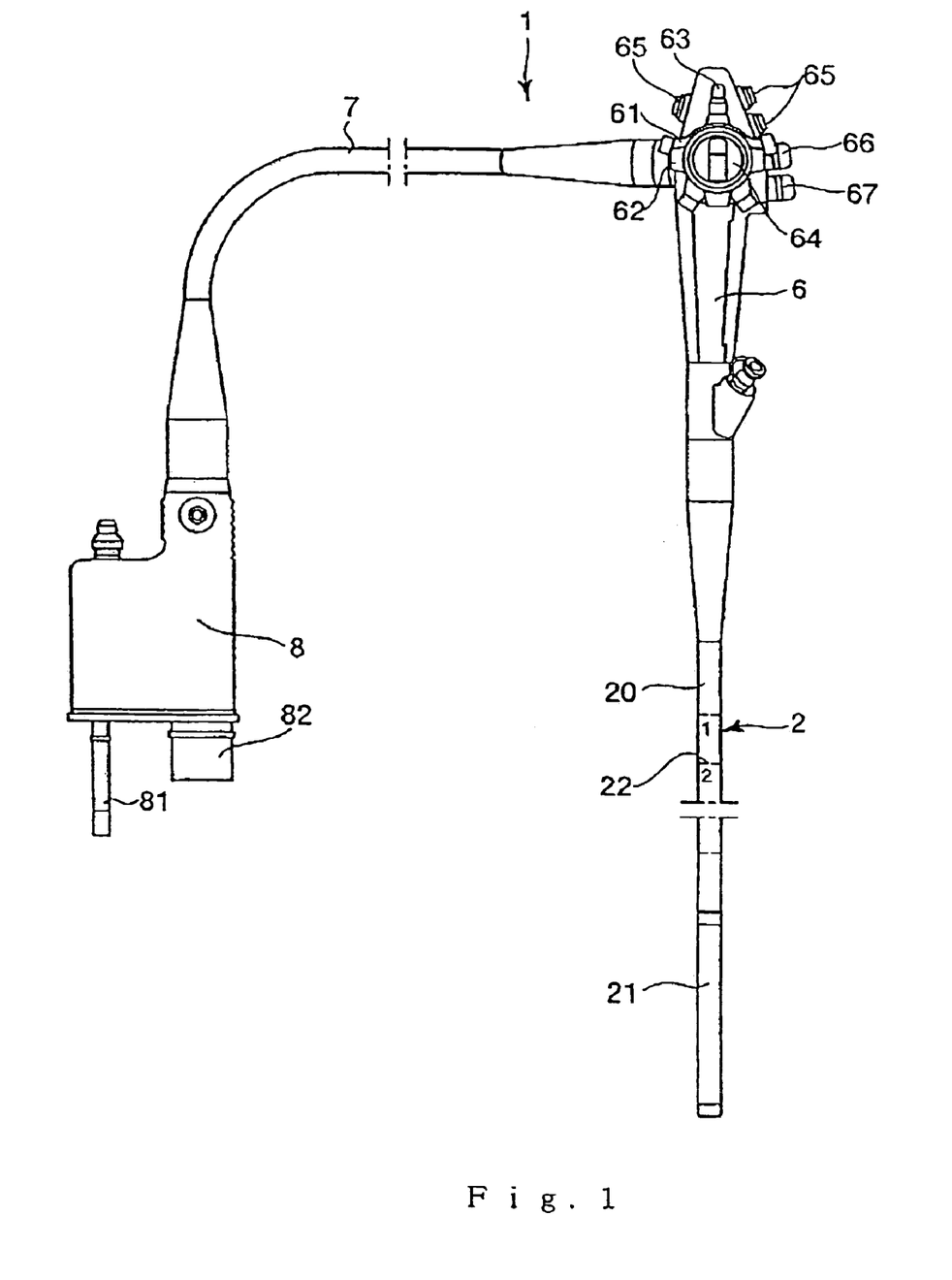
FIG. 1 is an overall view which shows an electronic endoscope (electronic scope)
Figure 2:
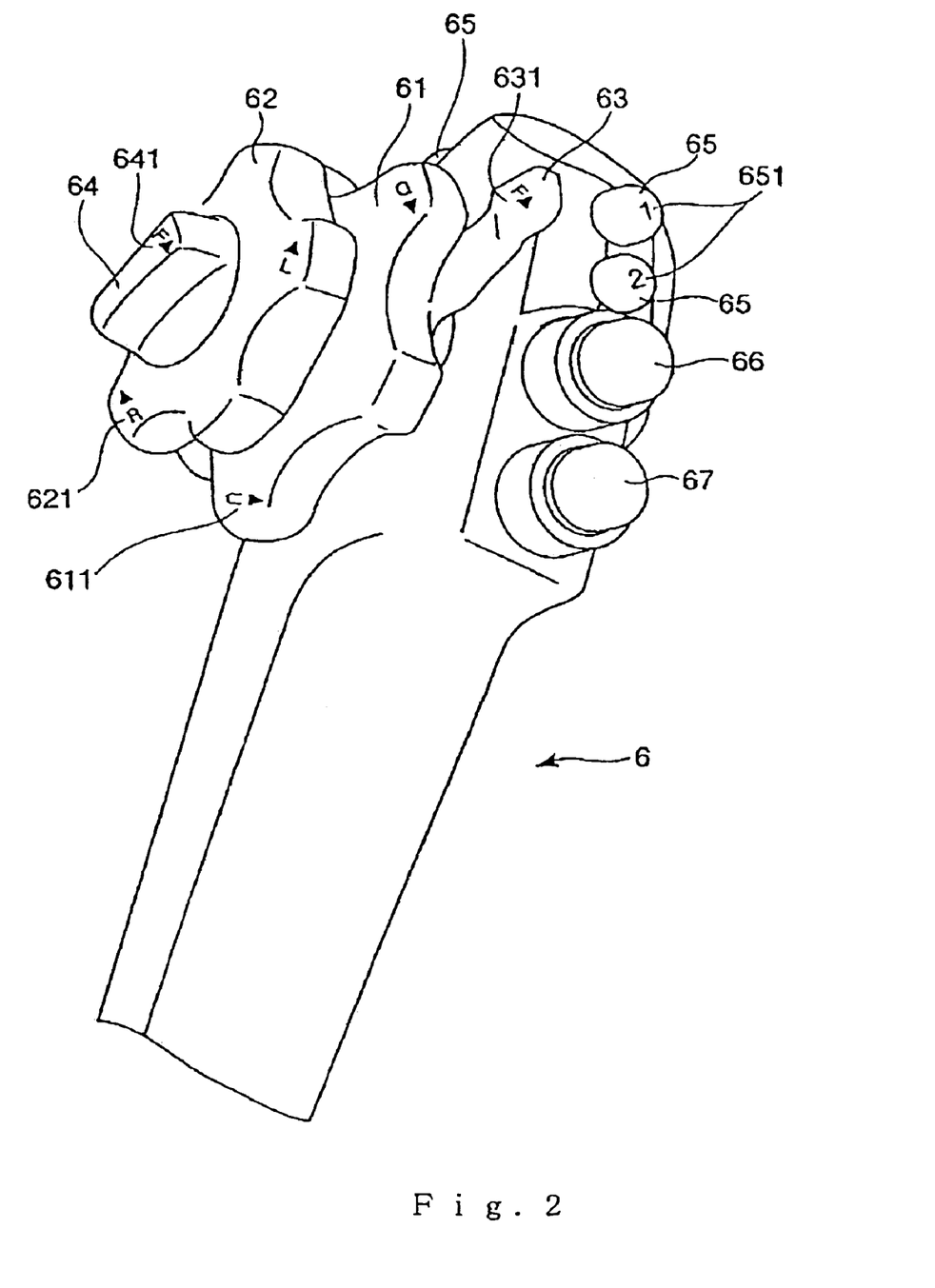
FIG. 2 is a perspective view which shows an operating section provided in the endoscope.
Figure 3:
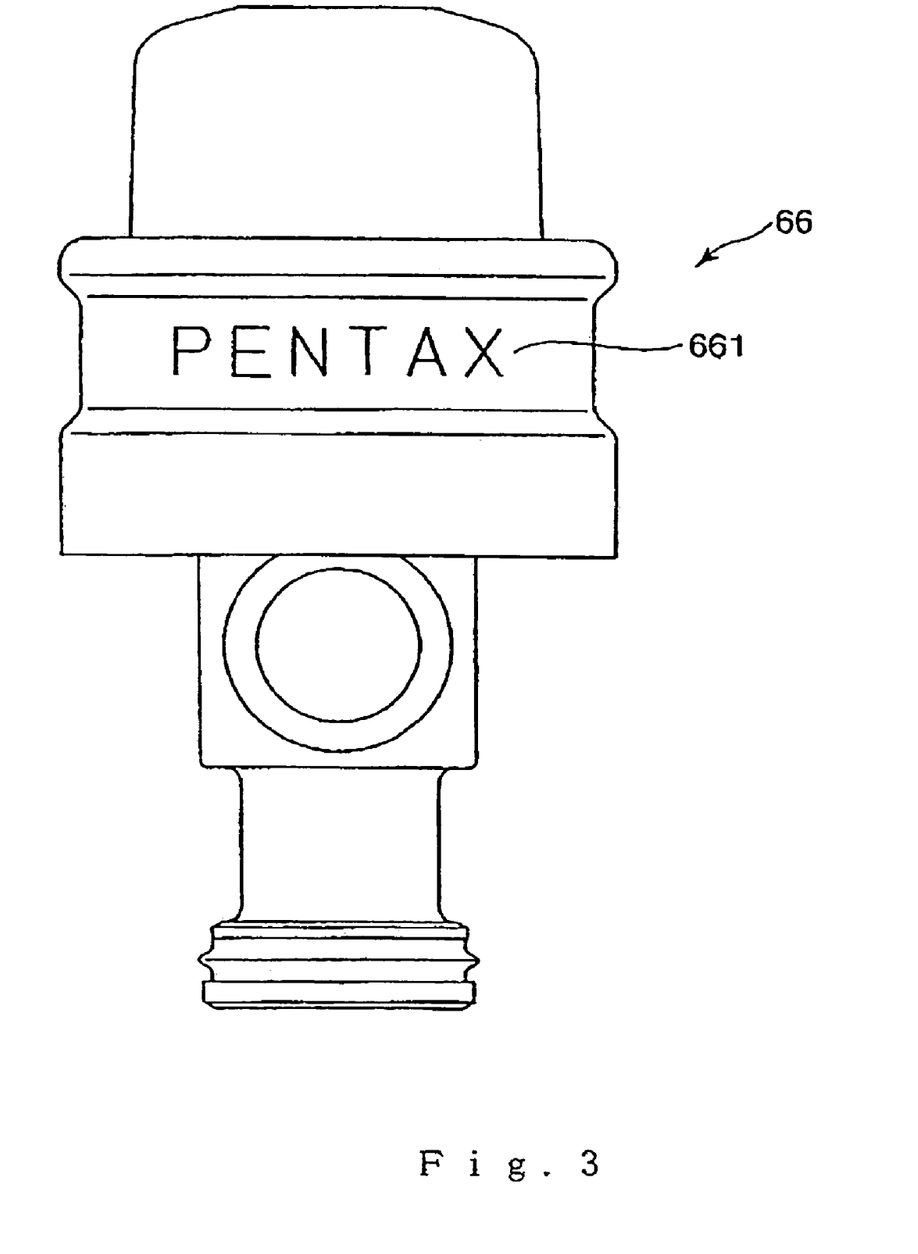
FIG. 3 is a side view which shows a suction button which has been removed from the electronic endoscope.

FIG. 1 is an overall view which shows an electronic endoscope (electronic scope), FIG. 2 is a perspective view which shows an operating section provided in the endoscope, and FIG. 3 is a side view which shows a suction button which has been removed from the electronic endoscope. In the following description, the upper side and the lower side in FIG. 1 will be referred to as "base or proximal" end or side and "tip or distal" end or side, respectively.

As shown in FIG. 1, the electronic endoscope 1 includes an elongated flexible tube (insertion section) 2 to be inserted into a body cavity of a living body; an operating section 6 provided on the base end of the flexible tube 2, which is gripped by an operator during an endoscopic examination to manipulate the whole of the electronic endoscope 1; a connecting flexible tube 7 connected at one end thereof to the operating section 6; and a light source plug section 8 provided on the other end of the connecting flexible tube 7.

The flexible tube 2 is used by being inserted into a body cavity. As shown in FIG. 1, the flexible tube 2 includes a flexible tube section 20 which is located at the base side of the flexible tube 2, and a bendable section 21 which is bendable in various directions and is provided at the tip of the flexible tube section 20.

As shown in FIG. 1, on the outer surface of the flexible tube 2, there is provided scale (visible maker) 22 which indicates the insertion depth of the flexible tube 2 into a body cavity. By providing such scale on the flexible tube 2, an operator can handle the flexible tube 2 while viewing the scale 22 when it is inserted into a body cavity so that the tip part of the flexible tube 2 can be guided to a target position reliably.

An imaging element (CCD) not shown in the drawings is provided inside the tip end portion of the bendable section 21 to take observation images of an observation site inside the body cavity. The imaging element is connected to an image signal connector 82 which is provided in the light source plug section 8 via an image signal cable (not shown in the drawings) which extends through the insides of the flexible tube 2, the operating section 6 and the connecting flexible tube 7.

On the tip side of the light source plug 8, a light source connector 81 is provided together with the image signal connector 82. By connecting the light source connector 81 and the image signal connector 82 to mating connectors of a light source processor (not shown in the drawings), the light source plug 8 is connected to the light source processor. Further, a monitor (not shown in the drawings) is connected to the light source processor through a cable.

Light emitted from the light source processor passes through the light source connector 81 and a light guide (not shown in the drawings) that runs inside the light source plug section 8, the connecting flexible tube 7, the operating section 6, the flexible tube 2 and the bendable tube 5, and then the light is irradiated from the tip end portion of the bendable section 21 toward the observation site for illumination. The light guide is formed from an optical fiber bundle which is comprised of a plurality of optical fibers formed from quartz, multi-component glass, or plastic or the like.

The reflected light from the observation site (which forms an image of the observation site) is received by the imaging element. Then, the imaging element outputs an image signal corresponding to the image formed on the imaging element by the reflected light. The image signal is transmitted to the light source plug section 8 via the image signal cable.

Then, in the light source plug 8 and the light source processor, the image signal is subjected to predetermined processing (such as signal processing, image processing, and the like), and then the processed signal is sent to the monitor. In this way, an image (electronic image) taken by the imaging element is displayed on the screen of the monitor in the form of a motion picture.

In the operating section 6, a first operating knob 61, a second operating knob 62, a first lock lever 63 and a second lock lever 64 are provided in a freely and independently rotatable manner.

By rotating each of the operating knobs 61 and 62, wires (not shown in the drawings) which are arranged inside the flexible tube 2 are pulled so that the bendable section 21 is bent in any of four directions, thereby enabling to change the direction of the bendable section 21.

As shown in FIG. 2, on the upper surface of the first operating knob 61, simplified symbols (visible makers) "ΔU" and "ΔD" 611 which indicate directions (up and down directions) toward which the bendable portion 21 is to be bent by the rotational operation of the first knob 61. Further, on the upper surface of the second operating knob 62, simplified symbols (visible makers) "ΔR" and "ΔL" 621 which indicate directions (right and left directions) toward which the bendable portion 21 is to be bent by the rotational operation of the second knob 62.

Further, by rotating each of the lock levers 63, 64 in the counter-clockwise direction, the bending state of the bending portion 21 (which is a resultant direction of the bending in the up and down directions and the bending in the right and left directions) can be locked (maintained). On the other hand, by rotating each of the lock levers 63, 64 in the clockwise direction, the bending state of the bending portion 21 which is locked in a bending state can be released.

On the upper surfaces of the respective lock levers 63, 64, there are provided simplified symbols (visible makers) "ΔF" 631, 641 which indicate the directions for releasing the locking states.

By carrying out rotational operations of the first operation knob 61, the second operation knob 62, the first lock lever 63 and the second lock lever 64 appropriately with looking the symbols 611, 621, 631 and 641, it is possible to bend the bending portion 21 toward a desired direction reliably, and it is also possible to secure (maintain) the bending state of the bending portion 21.

Further, as shown in FIG. 1, on the outer circumferential surface of the operating section 6, there are provided a suction button 65, an air and liquid supply button 67 and a plurality of control buttons 65 (in this embodiment, three buttons are provided).

By pushing each of the control buttons 65 in a state that the electronic endoscope 1 is connected to the light source processor (external apparatus), it is possible to remote-control various operations of the peripheral equipment such as the light source processor and the monitor. Examples of such various operations include switching between motion picture and still picture, ON/OFF of an electronic image filing system, ON/OFF of an imaging apparatus, ON/OFF of a recording apparatus of electronic images, and the like.

On the outer surface of each of the control buttons 65, there is provided a numeral (visible maker) 651 which indicates a peripheral equipment which is to be operated by pushing the button.

The suction button 66 and the air and liquid supply button 67 are provided for opening and closing a suction channel and an air and liquid supply channel (not shown in the drawings). These channels are formed so as to extend inside the light source plug 8, the connecting flexible tube 7, the operating section 6 and the flexible tube 2, and one ends of these channels are opened at the tip of the flexible tube 2 and the other ends thereof are opened at the light source plug 8.

Namely, before pushing the suction button 66 and the air and liquid supply button 67, the suction channel and the air and liquid supply channel are closed (that is, they are in a state that no fluid can pass therethrough). On the other hand, when the suction button 66 and the air and liquid supply button 67 are pushed, they are opened (that is, they are in a state that fluid can pass therethrough).

In this regard, it is to be noted that when the electronic endoscope 1 is used, a suction means is connected to the other end of the suction channel and an air and liquid supply means is connected to the other end of the air and liquid supply channel, respectively.

Accordingly, when the suction channel is in an open state, it is possible to suck body fluid and blood and the like within the body cavity from the tip of the flexible tube 2. Further, when the air and liquid supply channel is in an open state, it is possible to supply air and liquid into the body cavity from the tip of the flexible tube 2.

On the outer surfaces of the suction button 66 and the air and liquid supply button 67, there are also provided simplified symbols (visible makers) which indicate the functions of these buttons (not shown in the drawings).

By carrying out pushing operations of the control buttons 65, the suction button 66 and the air and liquid supply button 67 while looking and confirming the numerals 651 which are indicated on the outer surfaces of the control buttons 65 and the symbols indicated on the outer surfaces of the suction button 66 and the air and liquid supply button 67, it is possible to carry out desired treatments correctly.

As shown in FIG. 3, on the outer circumferential surface of the suction button 66, a manufacturer's mark (visible maker) 661 is indicated.

The present invention can be applied to these components which constitute the electronic endoscope 1 (such as the flexible tube 2, the first operating knob 61, the second operating knob 62, the first lock lever 63, the second lock lever 64, the control buttons 65, the suction button 66, and the air and liquid supply button 67 and the like). In this regard, it is to be noted that the present invention can be also applied to other components of the electronic endoscope 1 having any visible makers. Further, the present invention can be applied to accessories (attachments) of the endoscope 1 which are detachably attached to the endoscope 1.

Hereinbelow, a description will be made with regard to the typical example where the present invention is applied to the flexible tube 2.

Figure 4:
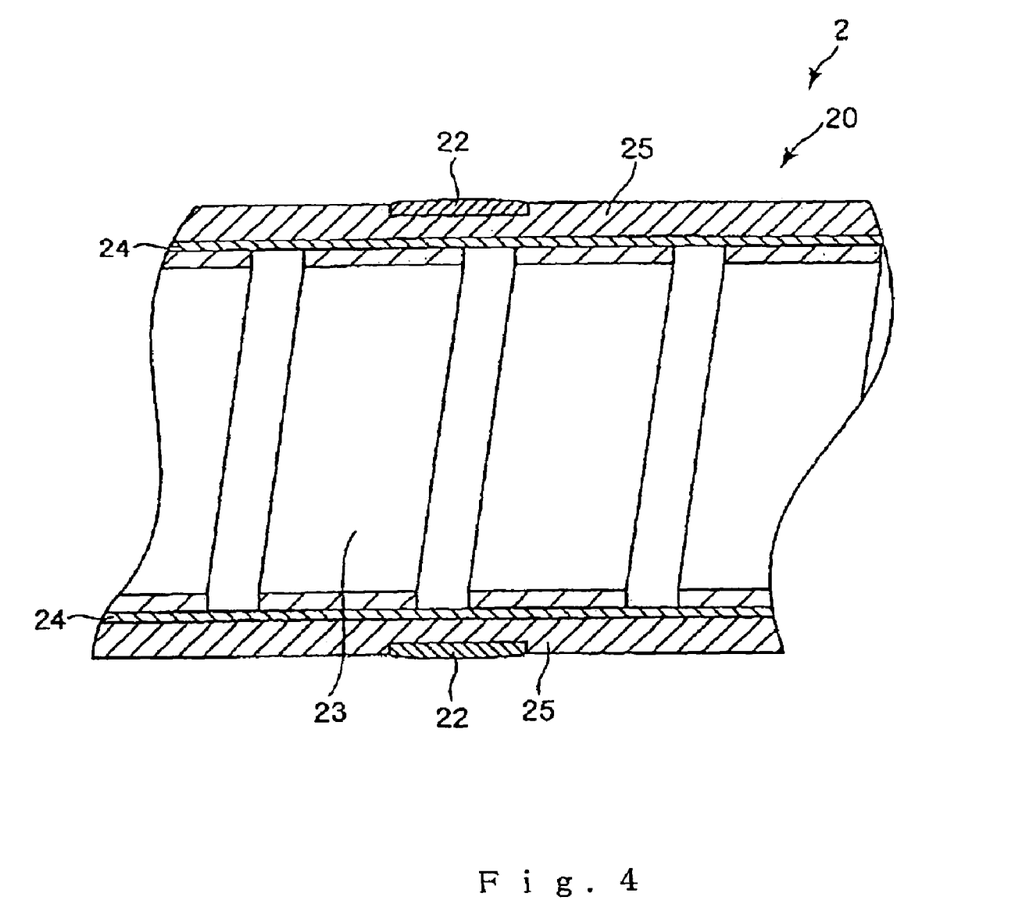
FIG. 4 is a longitudinal cross-sectional view of a flexible tube of a first embodiment of an endoscope according to the present invention.

FIG. 4 is a longitudinal sectional view of a flexible tube of a first embodiment of an endoscope according to the present invention.

The flexible tube 2 (flexible tube section 20) shown in FIG. 4 is constructed from a helical coil 23 which is formed by winding a flat band-shaped material helically, a reticular tube 24 which is formed by braiding metallic or non-metallic fine wires and covers the outer periphery of the helical coil 23, and an outer cover 25 which covers the outer periphery of the reticular tube 24.

The outer cover 25 is formed of a material containing a resin material as a major component and a color developing agent which is colored by irradiation with laser light.

The resin material for the outer cover 25 is not particularly limited to a specific material so long as it has flexibility. Examples of such a resin material includes polyolefin such as polyethylene, polypropylene, ethylene-propylene copolymer, ethylene-vinylacetate copolymer (EVA); cyclic polyolefin; modified polyolefin; polyvinyl chloride; polyvinylidene chloride; polystyrene; polyamide; polyimide; polyamide-imide; polycarbonate; poly-(4-methylpentene-1); ionomer; acrylic resin; polymethyl methacrylate; acrylonitrile-butadiene-styrene copolymer (ABS resin); acrylonitrile-styrene copolymer (AS resin); butadiene-styrene copolymer; polyoxymethylene; polyvinyl alcohol (PVA); ethylene-vinylalcohol copolymer (EVOH); polyester such as polyethylene terephthalate (PET), polybutylene terephthalate (PBT), polycyclohexane terephthalate (PCT)); polyether; polyether ketone (PEK); polyether ether ketone (PEEK); polyetherimide; polyacetal (POM); polyphenylene oxide; modified polyphenylene oxide; polysulfone; polyethersulfone; polyphenylene sulfide; polyalylate; aromatic polyester (liquid crystalline polymer); fluoro-based resin such as polytetrafluoroethylene, polyvinylidene fluoride; various thermoplastic elastomers such as polystyrene based elastomer, polyolefin based elastomer, polyvinylchloride-based elastomer, polyurethane-based elastomer, polyester-based elastomer, polyamide-based elastomer, polybutadiene-based elastomer, transpolyisoprene-based elastomer, fluororubber-based elastomer, chlorinated polyethylene-based elastomer and the like; various rubbers such as natural rubber (NR), olefin-based rubber (e.g. isoprene rubber (IR), butadiene-based rubber such as butadiene rubber (BR, 1,2-BR), styrene-butadiene rubber and the like, diene-based special rubber such as chloroprene rubber (CR), butadiene-acrylonitrile rubber (NBR) and the like, butyl rubber (TTR), ethylene-propylene rubber(EPM, EPDM), acrylic, rubber (ACM, ANM), and halogenated butyl rubber (X-IIR) and the like, urethane-based rubber such as urethane rubber (AU, EU), ether-based rubber such as hydrin rubber (CO, ECO, GCO, EGCO), polysulfide-based rubber such as polysulfide rubber (T), silicone rubber (Q), fluoro rubber (FKM, FZ), cholorinated polyethylene (CM) and the like; and copolymer, blended body or polymer alloy each having at least one of these materials mentioned above as a main ingredient. In this case, a mixture of one or two or more kinds of these materials may be employed. Among these materials, thermoplastic elastomer such as polyurethane-based elastomer, polystyrene-based elastomer, polyester-based elastomer, and polyolefin-based elastomer and the like, polyethylene, and polypropylene are particularly preferred as the resin material. This is because these resin materials have excellent chemical resistance, and therefore it is possible to improve durability against washing, sterilization and disinfection which are repeatedly performed on the electronic endoscope 1.

In this regard, so long as the internal elements arranged inside the flexible tube 2 can be protected, and so long as the flexibility and bendability of the flexible tube 2 are not impaired, there is no specific limitation on the average thickness of the outer cover 25, but it is preferred that the average thickness lies in the range of 100–3000 µm, and more preferably in the range of 200–1000 µm.

In the present invention, $TiN_xO_y$ (where, $0.1 \leq x \leq 1.0$, $0 \leq y \leq 1.9$) is used as the color developing agent. In connection with this, it is to be noted that if the value "x" is less than 0.1, there is a fear that color development will not occur appropriately. Further, it is difficult to contain N in the amount where "x" exceeds 1.0. On the other hand, if the value "y" exceeds 1.9 in the formula $TiN_xO_y$, it is not possible to obtain desired color tone.

Further, in the formula $TiN_xO_y$, it is preferred that weight ratio of O/N is 0.2 to 8, and more preferably 0.5 to 7.

The color developing agent maybe employed in various forms such as particles, granules, scales, pellets and the like. Among these forms, a color developing agent in the form of particles is particularly preferred. This makes it possible to disperse (mix) the color developing agent into the outer cover 25 (that is, the constituent material of the outer cover 25) uniformly.

When a color developing agent in the form of particles is used, there is no specific limitation on the average diameter of the particles. However, it is preferred that the average diameter is 10 µm or less, and more preferably 0.1 to 1 µm This makes it possible for the color developing agent to be dispersed into the outer cover 25 more uniformly.

The content of the color developing agent to be contained in the outer cover 25 varies depending on composition or properties (in particular, color tone or the like) of a resin material to be used. However, in order to make sufficient and satisfactory cooler development, it is preferred that the content of the cooler developing agent is in the range of 0.01 to 10 wt % and more preferably in the range of 0.01 to 1 wt %. If the content of the color developing agent is too small, there is a case that whiteness of a colored portion (scale 22) is lowered, so that the indication of the formed scale becomes unclear. On the other hand, if the content of the color developing agent exceeds the upper limit value, not only further increased effect can not be expected, but also there is a case that it becomes difficult to disperse the cooler developing agent into the outer cover 25 (the constituent material of the outer cover 25). In the present invention, by setting the content of the color developing agent as described above, it is possible to adjust color tone and intensity of color development after irradiation with laser light.

It is preferred that the color developing agent is dispersed in the outer cover 25 uniformly. However, the color developing agent may be unevenly distributed so that it is concentrated only in an area in the vicinity of the outer surface of the outer cover or it is existed only at a portion where a colored portion (scale 22) is to be formed and an area adjacent thereto.

Further, the composition of other constituent materials (that is, a compounding ratio of the components contained in the outer cover 25) may be uniform throughout the entire of the over cover 25, or may be changed depending on locations. For example, the compounding ratio of the components may be gradually changed along the thickness direction of the outer cover 25, that is a graded material may be used.

Furthermore, a coloring agent may be added or mixed into the constituent materials of the outer cover 25 as needed.

Examples of the coloring agent include various dyes such as nitro so dye, nitro dye, azo dye, stilbenazo dye, ketoimine dye, triphenylmethane dye, xanthene dye, acridine dye, quinoline dye, methane dye, thiazole dye, ndamine dye, azine dye, oxazine dye, thiazine dye, sulfur dye, aminoketone dye, anthraquinone dye, indigoid dye, quinophthalone, and anthrapyridone, and the like; various pigments, such as azo pigment, disazo pigment, phthalocyanine pigment, quinacridone pigment, perylene pigment, perinone pigment, dioxazine pigment, anthraquinone pigment, and isoindolinone pigment, and the like; and inorganic pigments such as lead sulfate pigment, titanate yellow pigment, iron oxide pigment, ultramarine blue pigment, cobalt blue pigment, chromium oxide green pigment, spinel green pigment, zinc yellow pigment, chrome vermilion pigment, chrome yellow pigment, chrome green pigment, cadmium yellow pigment, cadmium red pigment, carbon powder, zinc oxide, and, titanium oxide, and the like. These dyes or pigments may be employed alone or in combination with other dyes or pigments.

When the coloring agent is added to the constituent materials of the outer cover 25, the amount to be added (content) is not limited to a specific value, but it is preferred that the amount to be added is in the range of 0.001 to 1 parts by weight with respect to 100 parts by weight of the resin material and more preferably in the range of 0.01 to 0.1 parts by weight. If the content of the coloring agent is too small, there is a case that an effect by the addition of the coloring agent will not be exhibited depending on the kind of the coloring agent. On the other hand, if the content of the coloring agent is too much, there is a case that the outer cover 25 is damaged by the irradiation with laser light depending on the kind of the resin material.

Further, other additives may be added or mixed into the constituent materials of the outer cover 25 as needed.

Examples of such additives include inorganic filler, plasticizer, lubricant, various kinds of stabilizers (antioxidant, photo stabilizer, antistatic agent; blocking inhibitor); releasing agent, fir retardant, coupling agent, and X-ray contrast medium, and the like.

Further, examples of the inorganic filler include silicon compound such as silicon dioxide, mica, kaoline, blast furnace slag, silica sand, silica, talc and the like; calcium carbonate, alumina, glass fiber, glass flake, milled fiber, whisker of hardened zinc, whisker of potassium titanate, and the like.

Further, examples of the lubricant include stearic acid, behenic acid and esters or salts thereof, waxes such as carnauba wax, and polyethylene wax, and the like, various surfactants, and the like.

Furthermore, examples of the plasticizer include phthalic acid ester, phosphoric acid ester, and sebacin acid ester, and the like.

At a predetermined location on the outer peripheral surface of the outer cover 25, the scale (visible maker) 22 described above is provided as a colored portion which is formed by means of development of the color developing agent.

As shown in FIG. 1, in this embodiment, the scale 22 comprised of scale lines each having a width of 1 to 10 mm are provided along the elongated direction of the flexible tube 2 with a pitch of 10 cm. Of course, the pitch between the scale lines may be set as desired.

Instead of the scale 22 or in combination with the scale 22, other visible makers (colored portions) having different forms or patterns may be provided. Examples of such visible makers of the different forms or patterns include dotted pattern, lattice pattern, reticular pattern, numerals, letters, and symbols and the like that are visible with naked eyes. Two or more of them can be used together.

Next, a description will be made with regard to a method of forming such a scale (visible maker) 22.

The scale 22 is formed by irradiating a predetermined portion of the outer surface of the outer cover 25 containing a color developing agent with laser light to develop the color developing agent by the energy of the irradiation of the laser light.

Examples of the laser light that can be used for the irradiation includes carbon dioxide laser, He—Ne laser, ruby laser, semiconductor laser, argon laser, excimer laser, and YAG laser, and the like.

Among these lasers, YAG laser is particularly preferred, because the laser has a wavelength of 1.06 μm so that energy of the laser is hardly absorbed by the resin material which is a main constituent of the outer cover 25, thus burning and vaporization of the resin material is difficult to occur and therefore damage does not also occur.

A laser irradiation apparatus that can be used is not limited to a specific one, and know various laser irradiation apparatuses can be used. For example, scanning type, dot type and mask type laser irradiation apparatuses may be used.

Further, oscillation pattern may be either of continuous oscillation or pulse oscillation.

Before the irradiation of the laser light, the outer surface of the outer cover 25 has black color or dark color due to the presence of the $TiN_xO_y$ (which is inherently black). However, when the outer surface of the outer cover 25 is irradiated with laser light, the $TiN_xO_y$ (which is inherently black) is changed into $TiO_2$ (which is white) due to high temperature oxidative reaction, so that the color of the scale 22 (colored portion) becomes white or bright color. As described above, by using $TiN_xO_y$ as a color developing agent, it is possible to obtain a high contrast (extremely high difference in the brightness) between the scale (colored portion) 22 and a part other than the scale.

In this regard, it is preferred that the whiteness (L value) of the scale (colored portion) 22 is 60% or more, and more preferably 70% or more. When the whiteness is too low, it is not possible for the scale to provide a good visibility.

Further, by adding a coloring agent as described above into the constituent materials of the outer cover 25, it is possible to obtain increased contrast in the outer cover 25 between the scale and the part other than the scale.

As described above, the scale 22 is formed by means of development of the color developing agent caused by the irradiation with laser light. Therefore, peel-off, fade-away and color deterioration are difficult to occur in the thus formed scale 22. Further, since the thus formed scale 22 rises to have a height of 1 to 500 μm so that any concave portion is formed on the outer surface of the outer cover 25, chemical will not remain in the portion of the scale 22 when the electronic endoscope 1 is sterilized or disinfected, thereby enabling to prevent or suppress the outer cover 25 from being deteriorated.

Further, according to the present invention, it is not necessary to have an ink drying process which is required to form a scale 212 onto the outer surface of the outer cover 25 by printing. Therefore, the present invention has an advantage in that the scale 22 can be formed in a shorter time.

In the embodiment described above, the outer cover 25 is formed into a single layer, but in the present invention, a part of or the entire of the outer cover 25 in the longitudinal direction thereof may be formed from a laminate structure comprised of a plurality of layers. In this modification, it is sufficient that at least the outermost layer has the same structure as the outer cover 25 of this embodiment.

<Second Embodiment>

Hereinbelow, a description will be made with regard to the second embodiment of the flexible tube of the present invention.

Figure 5:
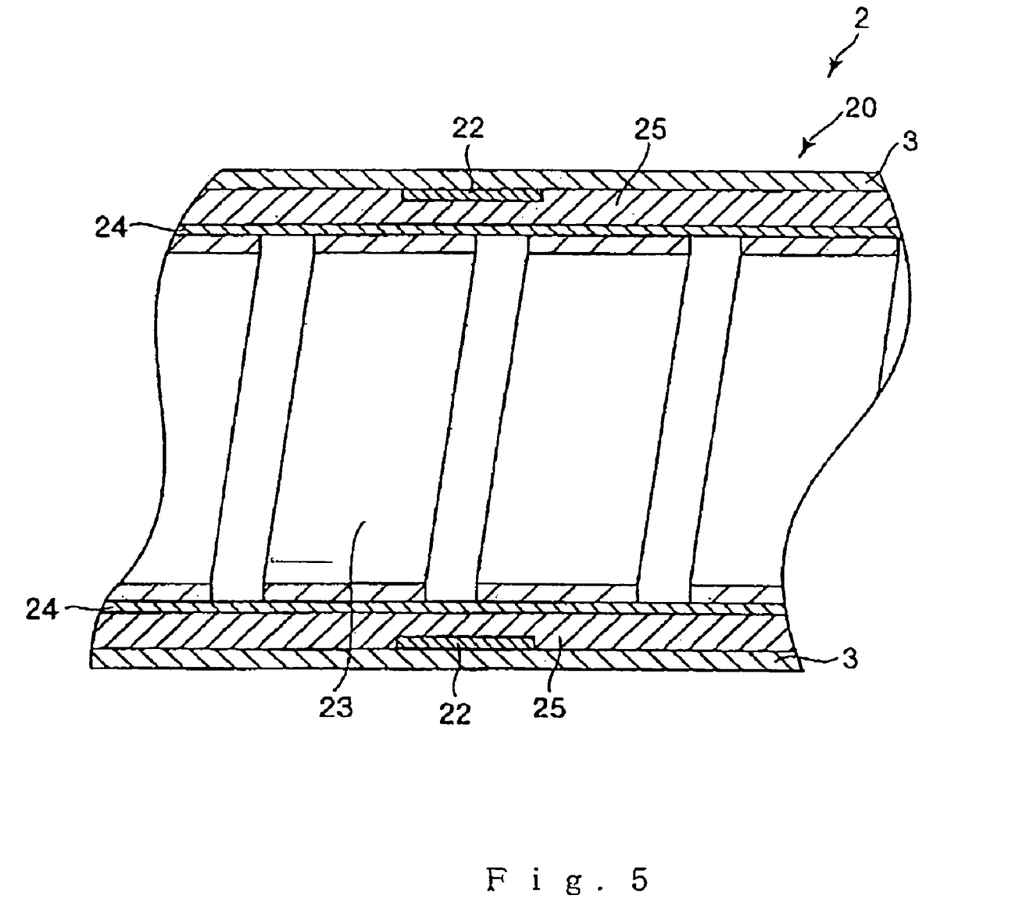
FIG. 5 is a longitudinal cross-sectional view of a flexible tube of a second embodiment of the endoscope according to the present invention.

FIG. 5 is a longitudinal cross-sectional view which shows a second embodiment of the flexible tube 2 of the present invention.

In the following description, the second embodiment will be described by focusing on the differences between the first and the second embodiments, and a description to the common structures will be omitted.

The second embodiment is the same as the first embodiment excepting that the flexible tube 2 of the second embodiment is provided with a coating layer 3 which covers the entire of the outer surface of the outer cover 25.

The coating layer 3 functions as a protective layer of the outer cover 25, so that peel-off, fade-away and color deterioration of the scale 22 (colored portion) can be prevented reliably. Further, it is also possible to prevent the colored portion from being peeled off or damaged even if that portion is scratched.

The coating layer 3 has transparency through which the scale 22 portion can be seen. Therefore, it is possible to prevent visibility of the scale 22 from being lowered.

The constituent material of the coating layer 3 is not particularly limited if it has relatively high transparency. Examples of such a material include various thermoplastic elastomers such as polyurethane-based elastomer, polystyrene-based elastomer, polyester-based elastomer, polyolefin-based elastomer, polyethylene, polypropylene, polyurethane, and the like. These materials can be used alone or in combination with two or more of them. Among these materials, polyurethane-based thermoplastic elastomer, polyester-based thermoplastic elastomer, and polyurethane are particularly preferred for the constituent material of the coating layer 3, because these materials have high transparency and high solubility (adhesion) with the constituent material of the outer cover 25.

When the coating layer 3 is to be formed, the scale 22 may be formed before the coating layer 3 is formed or after the coating layer 3 has been formed. In the latter case, laser light is irradiated onto the outer surface of the outer cover 25 passing through the coating layer 3. Therefore, the coating layer 3 should have transparency as described above and have a property through which the laser light for forming the scale 22 can be passed.

The optical properties (characteristics) of the coating layer 3 are determined by various conditions of the coating layer 3 such as transparency and refractive index of the constituent material of the coating layer 3 and thickness of the coating layer 3 and the like.

The average thickness of the coating layer 3 is not particularly limited to a specific value, but it is preferred that the thickness is in the range of 0.01 to 0.8 mm, and more preferably in the range of 0.02 to 0.1 mm. If the thickness is the coating layer 3 is too large, there is a case that visibility of the scale 22 is lowered depending on the transparency and reflective index of the constituent material of the coating layer 3. On the other hand, if the thickness of the coating layer 3 is too small, there is a case that a part of the coating layer 3 is peeled-off or chipped off due to friction or impact, thus resulting in the case that the protection function for the scale 22 is lowered.

A method of forming the coating layer 3 is not limited, and various methods can be used. Examples of such methods include a method in which the coating layer 3 is formed together with the outer cover 25 by means of multi-color molding, a method using injection molding (including an inner molding and an outer molding), a coating method (e.g. spray coating), and a method using a thermal shrinkage tube (film) in which the thermal shrinkage tube attached to the outer cover 25 is heated to be shrank to form the coating layer 3.

In this embodiment, it is to be noted that it is not necessary that the optical properties of the coating layer 3 mentioned above are exhibited in the entire of the coating layer 3. It is sufficient that at least a part of the coating layer 3 which covers the scale 22 has the optical properties described above.

Further, although it is preferred that the coating layer 3 covers the entire of the outer surface of the outer cover 25 as described above, such a coating layer 3 may be formed so as to cover only a portion where the scale 22 is formed and its vicinity.

In the foregoing, descriptions are made with regard to the components of an endoscope according to the present invention based on the first and second embodiments shown in the drawings. However, the present invention is not limited to these embodiments.

For example, in the present invention, the whole of the component is formed of a resin material containing a color developing agent.

Further, a part of the component near the outer surface thereof may be formed from a material comprised of a silicone compound such as alkoxysilane or hydrolysate thereof and a color developing agent.

Furthermore, the endoscope of the present invention is not limited to an electronic endoscope. The present invention may be applied to optical endoscopes (fiber scopes). Further, the present invention may also be applied to endoscopes for industrial use other than endoscopes for medical use.

EXAMPLES

Hereinbelow, a description will be made with regard to the practical examples of the present invention.

The present invention may be applied to various components of an endoscope on which visible makers are indicated. However, the following examples are directed to the case where the present invention is applied to a flexible tube of an electronic endoscope due to the following reasons. (1) If a visible maker attached to a flexible tube is peeled off in a body cavity, it remains within the body cavity. Since this may cause a serious problem, a visible maker indicated on the flexible tube is particularly important. (2) An outer cover of a flexible tube of an endoscope is required to have particularly excellent durability, since it is repeatedly subjected to sterilization and disinfection. For these reasons, in the following examples, endoscopes having flexible tubes each having a visible maker were manufactured and their properties were tested.

Example 1

First, a helical coil having an outer diameter of 9 mm and an inner diameter of 7 mm was manufactured by winding a flat band-shaped stainless steal member having a width of 3.2 mm. Then, a joint ring was attached to the tip of the helical tube. Thereafter, the helical tube was covered with a reticular tube which was formed by braiding wire bundles each comprised of ten stainless steel fine wires each having a diameter of 0.08 mm, to obtain a core member having a length of 1.5 m.

Next, the core member was covered with an outer cover (having an average thickness of 0.4 mm) which is formed of a polyurethane-based elastomer ("PANDEX", a product name of DIC Bayer Polymer Ltd.) containing $TiN_{0.3}O_{1.3}$ (color developing agent) by means of extrusion molding.

The color developing agent $TiN_{0.3}O_{1.3}$ was powder comprised of particles having an average diameter of 0.4 μm. Further, the content of the $TiN_{0.3}O_{1.3}$ in the outer cover (constituent materials of the outer cover) was 0.1 weight percent.

Then, thus prepared outer cover was irradiated with YAG laser to form a scale. In this way, a flexible tube as shown in FIG. 4 was obtained.

Thereafter, using the thus obtained flexible tube, an electronic endoscope (upper gastrointestinal endoscope) as shown in FIG. 1 was manufactured.

Examples 2 to 6

Electronic endoscopes equipped with flexible tubes were manufactured in the same manner as Example 1 excepting that the conditions of the color developing agent were changed as shown in Table 1.

Example 7

A core member was manufactured in the same manner as the Example 1, and then the core member was covered with an outer cover. Further, a coating layer, was formed onto the outer periphery of the outer cover using an urethane-based coating agent. The average thickness of the coating layer was 0.03 mm.

Then, a scale was formed by irradiation with YAG laser light to obtain a flexible tube as shown in FIG. 5.

Thereafter, using the thus obtained flexible tube, an electronic endoscope (upper gastrointestinal endoscope) as shown in FIG. 1 was manufactured.

Comparative Example 1

A core member was formed in the same manner as that of Example 1, and then the core member was covered with an outer cover (having an average thickness of 0.4 mm) which is formed of a polyurethane-based elastomer ("PANDEX", a product name of DIC Bayer Polymer Ltd.) containing no color-developing agent by means of extrusion molding.

Then, a scale was formed on the outer surface of the outer cover by printing with polyurethane-based paint (ink), to obtain a flexible tube.

Thereafter, using the thus obtained flexible tube, an electronic endoscope (upper gastrointestinal endoscope) as shown in FIG. 1 was manufactured.

Comparative Example 2

A core member was formed in the same manner as that of Example 1, and then the core member was covered with an outer cover (having an average thickness of 0.4 mm) which is formed of a polyurethane-based elastomer ("PANDEX", a product name of DIC Bayer Polymer Ltd) containing no color developing agent by means of extrusion molding.

Then, scale in the form of grooves was formed on the outer surface of the outer cover by means of laser processing using YAG laser, to obtain a flexible tube.

Thereafter, using the thus obtained flexible tube, an electronic endoscope (upper gastrointestinal endoscope) as shown in FIG. 1 was manufactured.

Evaluation

The following evaluation tests I to III were conducted for each of the electronic endoscopes of Examples 1 to 7 and Comparative Examples 1 and 2.

Evaluation Test I (Whiteness)

The whiteness (L value) at the portion where the scale is formed was measured for each of the electronic endoscopes of Examples 1 to 7 and Comparative Examples 1 and 2 using a whiteness checker (NW-1 which is a product name of Nippon Denshoku Industries Co., Ltd.). The evaluation was made in accordance with the following two ranks.

A: Equal to or greater than 60%

B: Less than 60%

Evaluation Test II (Visibility)

In each of the electronic endoscopes of Examples 1 to 7 and Comparative Examples 1 and 2, the scale was observed with naked eyes to determine its visibility and evaluate it in accordance with the following four ranks.

A: Excellent

B: Good

C: Poor

D: No-good (NG)

Evaluation Test III (Durability)

Each of the electronic endoscopes of Examples 1 to 7 and Comparative Examples 1 and 2 was subjected to sterilization using a sterilization apparatus for strong acid water for 300 cycles. The sterilization was carried out under the conditions that pH was 2.5±0.2, oxidation-reduction potential was 1100 mV, and available chlorine concentration of 50 ppm. After the sterilizations of 300 cycles, the scale of each of the flexible tubes of the endoscopes was observed with naked eyes, and evaluation was made in accordance with the following four ranks.

A: Scale was kept in a clear state, and no deterioration was observed in the outer cover.

B: Scale became slightly unclear, but no deterioration was observed in the outer cover.

C: Scale became unclear, and roughness was observed around the scale of the outer cover.

D: Scale could not be seen, and considerable degree of roughness was observed around the scale of the outer cover.

The results of the evaluation tests I to III are shown in Table 1 together with the conditions of the color developing agents and the kinds of the resin materials of the outer covers.

TABLE 1

| | | | Outer Cover | | | | | | |
|---|---|---|---|---|---|---|---|---|---|
| | | $TiN_xO_y$ | | | | | | | |
| | x | y | Average Particle Size [μm] | Content [wt %] | Resin Material | Coating Layer | Evaluation I | II | III |
| Example 1 | 0.3 | 1.3 | 0.4 | 0.1 | TPU | None | B | A | A |
| Example 2 | 0.3 | 1.3 | 0.4 | 0.5 | TPU | None | B | A | A |
| Example 3 | 0.3 | 1.3 | 0.4 | 1.0 | TPU | None | B | A | A |
| Example 4 | 0.3 | 1.3 | 0.4 | 3.0 | TPU | None | B | A | A |
| Example 5 | 0.3 | 1.3 | 0.4 | 5.0 | TPU | None | B | A | A |
| Example 6 | 0.3 | 1.3 | 0.4 | 10.0 | TPU | None | B | A | A |
| Example 7 | 0.3 | 1.3 | 0.4 | 1.0 | TPU | PU | B | A | A |
| Comp. Ex. 1 | | | None | | TPU | None | B | A | C |
| Comp. Ex. 2 | | | None | | TPU | None | C | C | C |

TPU Polyurethan based thermoplastic elastomer
PU Polyurethane

As shown in Table 1, in each of the electronic endoscopes manufactured In Examples 1 to 7, the whiteness (L value) of the scale was high, the visibility was extremely excellent, and the scale was kept in a clear state after the 300 cycle sterilizations in accordance with the Evaluation Test III.

On the other hand, the electronic endoscope manufactured in Comparative Example 1 the whiteness (L value) of the scale was high and the visibility was excellent just after manufacture thereof. However, the durability was poor, so that after the 300 cycle sterilizations the scale was peeled off by wiping up it with ethanol.

Further, the electronic endoscope manufactured in Comparative Example 2, the whiteness (L value) of the scale was low and the visibility was no-good. Further, the durability was no-good, so that after the 300 cycle sterilizations considerable degree of roughness was observed around the scale of the outer cover.

As described above, according to the present invention, it is possible to obtain extremely high contrast between the colored portion and a part other than the colored portion, thus enabling to provide excellent visibility. Further, peel-off, fade-away and color deterioration of the colored portion as well as deterioration of the outer cover near the colored portion resulted from the formation of the colored portion are also difficult to occur.

Further, by providing the coating layer, the colored portion can be protected, so that peel-off, fade-away and color deterioration of the colored portion can be prevented more reliably.

Furthermore, an endoscope equipped with the component according to the present invention can realize good operability due to the clear visible maker.

Finally, it is to be understood that many changes and additions may be made to the embodiments described above without departing from the scope and spirit of the invention as defined in the following claims.

Further, it is also to be understood that the present disclosure relates to subject matter contained in Japanese Patent Application No. 2002-369059 (filed on Dec. 19, 2002) which is expressly incorporated herein by reference in its entirety.

What is claimed is:

1. An endoscope, comprising:
   an operating section provided with a plurality of components for manipulating the endoscope; and
   an elongated flexible tube to be inserted into a body cavity of a living body, the flexible tube having a base end connected to the operating section, and the flexible tube including an outer cover having an outer surface and made of thermoplastic elastomer, the outer cover having black or dark color by the presence of a color developing agent comprising $TIN_xO_y$ (where, $0.1 \leq x \leq 1.0$, $0 \leq y \leq 1.9$) which is changed into $TiO_2$ having white color by irradiation with laser light, wherein the outer surface of the outer cover being formed with a colored portion having white or bright color, the colored portion being formed by means of development of the color developing agent due to irradiation with the laser light, and wherein the color developing agent is contained at least in the vicinity of the outer surface of the outer cover, and the content of the color developing agent contained in the outer cover is 3.0 to 10 weight percent of the outer cover.

2. The endoscope as claimed in claim 1, wherein the color developing agent is in the form of particles.

3. The endoscope as claimed in claim 2, the average particle size of the particulate color developing agent is 10 μm or less.

4. The endoscope as claimed in claim 1, wherein the degree of whiteness (L value) of the colored portion after the irradiation with laser beam is 60% or more.

5. The endoscope as claimed in claim 1, further comprising a coating layer which is provided so as to cover at least the colored portion and which has transparency through which the colored portion can be seen.

6. The endoscope as claimed in claim 1, further comprising a coating layer which is provided so as to cover at least the colored portion and which has transparency through which the colored portion can be seen, and through which the laser light can be passed.

7. The endoscope as claimed in claim 1, wherein the colored portion is used as a visible marker.

8. The endoscope according to claim 1, wherein the components of the operating section include knobs, levers and/or buttons, and at least one of these components having an outer surface made of a resin material, the component having black or dark color by the presence of a color developing agent comprising $TiN_xO_y$ (where, $0.1 \leq x \leq 1.0$, $0 \leq y \leq 1.9$) which is chanced into $TiO_2$ having white color by irradiation with laser light, wherein the outer surface of the component being formed with a colored portion having white or bright color, the colored portion being formed by means of development of the color developing agent due to irradiation with laser light, and wherein the color developing agent is contained at least in the vicinity of the outer surface of the component, and the content of the color developing agent contained in the component is 3.0 to 10 weight percent of the component.

9. The endoscope as claimed in claim 8, wherein the colored portion is used as a visible marker.

10. An endoscope, comprising:
    an operating section provided with a plurality of components for manipulating the endoscope; and
    an elongated flexible tube to be inserted into a body cavity of a living body, the flexible tube having a base end connected to the operating section,
    wherein the components of the operating section include knobs, levers and/or buttons, and at least one of these components having an outer surface made of a resin material, the component having black or dark color by the presence of a color developing agent comprising $TiN_xO_y$ (where. $0.1 \leq x \leq 1.0$, $0 \leq y \leq 1.9$) which is changed into $TiO_2$ having white color by irradiation with laser light, wherein the outer surface of the component being formed with a colored portion having white or bright color, the colored portion being formed by means of development of the color developing agent due to irradiation with laser light, and wherein the color developing agent is contained at least in the vicinity of the outer surface of the component, and the content of the color developing agent contained in the component is 3.0 to 10 weight percent of the component.

11. The endoscope as claimed in claim 10, wherein the colored portion is used as a visible marker.

* * * * *